(12) United States Patent
Schmid et al.

(10) Patent No.: US 10,967,039 B2
(45) Date of Patent: Apr. 6, 2021

(54) PROCESS FOR PREPARING STEALTH NANOPARTICLES

(71) Applicant: SINTEF TTO AS, Trondheim (NO)

(72) Inventors: Ruth Schmid, Tiller (NO); Per Stenstad, Trondheim (NO); Yrr Morch, Trondheim (NO); Heidi Johnsen, Trondheim (NO)

(73) Assignee: SINTEF TTO AS, Trondheim (NO)

( * ) Notice: Subject to any disclaimer, the term of this patent is extended or adjusted under 35 U.S.C. 154(b) by 0 days.

(21) Appl. No.: 14/894,495

(22) PCT Filed: May 28, 2014

(86) PCT No.: PCT/EP2014/061144
§ 371 (c)(1),
(2) Date: Nov. 27, 2015

(87) PCT Pub. No.: WO2014/191502
PCT Pub. Date: Dec. 4, 2014

(65) Prior Publication Data
US 2016/0129132 A1   May 12, 2016

(30) Foreign Application Priority Data

May 28, 2013 (EP) .................................. 13169557

(51) Int. Cl.

| | |
|---|---|
| *A61K 38/06* | (2006.01) |
| *C08F 283/06* | (2006.01) |
| *A61K 9/51* | (2006.01) |
| *C08F 2/22* | (2006.01) |
| *A61K 47/69* | (2017.01) |
| *A61K 47/58* | (2017.01) |
| *A61K 47/60* | (2017.01) |
| *C08F 222/32* | (2006.01) |

(52) U.S. Cl.
CPC ............ *A61K 38/06* (2013.01); *A61K 9/5138* (2013.01); *A61K 9/5146* (2013.01); *A61K 9/5192* (2013.01); *A61K 47/585* (2017.08); *A61K 47/60* (2017.08); *A61K 47/6933* (2017.08); *A61K 47/6935* (2017.08); *C08F 2/22* (2013.01); *C08F 283/06* (2013.01); *C08F 222/324* (2020.02)

(58) Field of Classification Search
CPC .... A61K 38/06; A61K 47/6933; A61K 47/60; A61K 47/585; A61K 47/6935; A61K 9/5192; A61K 9/5146; A61K 9/5138; C08F 2/22; C08F 283/06; C08F 222/324; C08F 2222/324
See application file for complete search history.

(56) References Cited

U.S. PATENT DOCUMENTS

| | | | |
|---|---|---|---|
| 2002/0034474 A1 | 3/2002 | Sabel et al. | |
| 2003/0082235 A1* | 5/2003 | Cohn .................... | C08G 63/664 424/486 |
| 2008/0138418 A1 | 6/2008 | Lee et al. | |
| 2008/0182776 A1 | 7/2008 | Lee et al. | |
| 2009/0297613 A1 | 12/2009 | Ringes et al. | |
| 2010/0015165 A1 | 1/2010 | Landfester et al. | |
| 2010/0104645 A1 | 4/2010 | Ali et al. | |
| 2010/0216804 A1 | 8/2010 | Zale et al. | |
| 2011/0195125 A1 | 8/2011 | McDonough et al. | |
| 2011/0224723 A1 | 9/2011 | Lee et al. | |
| 2012/0132346 A1* | 5/2012 | Chen .................... | B60C 1/0016 156/110.1 |

FOREIGN PATENT DOCUMENTS

| | | |
|---|---|---|
| WO | WO 06/016020 | 2/2006 |
| WO | WO 11/041897 | 4/2011 |
| WO | WO 2014/191502 | 12/2014 |

OTHER PUBLICATIONS

Gref et al. ("The controlled intravenous delivery of drugs using PEG-coated sterically stabilized nanospheres", 1995).*
Wu et al. ("Well-Defined Poly(butyl cyanoacrylate) Nanoparticlesvia Miniemulsion Polymerization", 2009).*
Trivedi et al. ("Nanomicellar formulations for sustained drug delivery: strategies and underlying principles", 2010).*
Huang et al. ("Synthesis of high loading and encapsulation efficient paclitaxel-loaded poly(n-butyl cyanoacrylate) nanoparticles via miniemulsion", 2007).*
Landfester, Macromol, Rapid Comm 2001 (22) 896-936.
Landfester, et al, Macromolecules 1999 (32) 5222-5228.
Chaudhari, et al., Targeting Efficiency and Biodistribution of Zoledronate Conjugated Docetaxel Loaded Pegylated PBCA Nanoparticles for Bone Metastasis. Adv. Funct. Mater. 2012, 22, k4101-4114.
Nicolas, J. & Couvreur, Patrick, Synthesis of poly(alkyl cyanoacrylate)-based colloidal nanomedicines. Wiley Interdiscipl. Rev. Nanomed. Nanobiotechnol, 2009 1 111-127.
Crespy, Daniel, et al., Miniemulsion polymerization as a versatile tool for the synthesis of functionalized polymers. Beilstein J. Org. Chem 2010, 6, 1132-1148.
Peracchia, M.T., et al., Development of sterically stabilized poly(isobutyl 2-cyanoacrylate) nanoparticles by chemical coupling of poly(ethylene glycol). 1997, Journal of Biomedical Materials Research, vol. 34, 317-326.
Yordanov, G. & Dushkin, C., Recent Advances in the Preparation of Drug-Loaded Poly (Alkyl Cyanoacrylate) Colloidal Particles for Cancer Treatment: Nanoprecipiatation vs. Polymerization. University of Sofia, Faculty of Chemistry.
Zhang, Yu, et al., Preparation, Characterization and biocompatibility of Poly(ethylene glycol)-poly(n-butyl cyanoacrylate) nanocapsules with oil core via miniemulsion polymerization. 2008 European Polymer Journal 44, 1654-1661.

(Continued)

*Primary Examiner* — Aradhana Sasan
*Assistant Examiner* — Quanglong N Truong
(74) *Attorney, Agent, or Firm* — Fox Rothschild LLP

(57) ABSTRACT

A process for the preparation of targeting nanoparticles of a poly(alkyl cyanoacrylate) homopolymer or copolymer, wherein said method comprises, in a single step, the anionic polymerisation of an oil-in-water miniemulsion as herein defined. The invention also relates to nanoparticles produced from said process and to their use in medicine.

13 Claims, No Drawings

(56) References Cited

OTHER PUBLICATIONS

Asua, Jose M., Miniemulsion Polymerization, 2002 Prog. Polym. Sci. 27, 1283-1346.
El-Aasser, Mohamed S. & Sudol, E. David, Miniemulsions: Overview of Research and Applications. Jan. 2004, JCT Research, vol. 1, No. 1.
Antonietti, Markus, et al., Polyreactions in miniemulsions, 2002 Prog. Polym. Sci. 689-757.
Chiellini, Federica, et al., Micro/nanostructured polymeric systems for biomedical and pharmaceutical applications, 2008 Nanomedicine 3(3), 367-393.
Landfester, Katharina, et al., Formulation and Stability Mechanisms of Polymerizable Miniemulsions, 1999 Macromolecules 32, 5222-5228.
Yordanov, G. et al., Recent Advances in the Preparation of Drug-Loaded Poly (Alkyl Cyanoacrylate) Colloidal Particles for Cancer Treatment: Nanoprecipiatation vs. Polymerization, Rev. Nanomed. Nanobiotechnol., 2009 (1) 111-127.
Crespy, D. & K. Landfester, Beilstein J. Org. Chem., 2010 (6) 1132-1148.
Storm, et al., Adv Drug Deliv Rev. 1995, 17, 31-48.
Stolnik, Illum, et al., Adv Drug Deliv Rev. 1995, 16, 195-214.
Reis, C.P., et al., Nanomedicine 2006 (2) 8-21.
Chiellini, F., et al., Nanomedicine 2008 (3) 367-393.
El-Aasser, et al., JCT Research 2004 (1) 21-31.
Asu, J.M., Prog. Polym. Sci. 2002 (27) 1283-1346.
Antonietti, M., et al. Proc. Poly. Sci. 2002 (27) 689-757.

\* cited by examiner

PROCESS FOR PREPARING STEALTH NANOPARTICLES

This invention relates to a process for preparing nanoparticles. In particular, it relates to a process for preparing targeting stealth nanoparticles. The invention also relates to the nanoparticles themselves, pharmaceutical compositions comprising the nanoparticles and to their use in drug delivery and molecular imaging.

BACKGROUND OF THE INVENTION

The use of nanotechnology in medicine offers many exciting possibilities with potential in a number of medicinal applications envisaged. In particular, nanomedicine is expected to lead to big improvements in the treatment of complex diseases. Two areas in which the use of nanoparticles has begun to demonstrate particular value are drug delivery and molecular imaging.

Nanoparticles for the delivery of therapeutic agents have the potential to circumvent many challenges associated with traditional delivery approaches, including lack of patient compliance to prescribed therapy, adverse side effects and poor clinical efficacy due to lack of targeted delivery. Important technological advantages of nanoparticles for drug delivery include the ability to deliver water-insoluble and unstable drugs, incorporation of both hydrophobic and hydrophilic therapeutic agents and the ability to utilise various routes of administration. Nanoparticle delivery systems may also facilitate targeted drug delivery and controlled release applications, enhancing drug bioavailability at the site of action, reducing dosing frequency and overall dosage size, thereby minimising side effects. As a result of these potential advantages, a variety of nanoparticulate systems have been investigated for use as drug delivery vehicles. These include polymeric micelles, polymers, liposomes, low-density lipoproteins, solid-lipid nanoparticles, dendrimers, hydrophilic drug-polymer complexes and ceramic nanoparticles.

Nanoparticle-based imaging agents may have increased circulation time and altered water-solubility, thereby avoiding rapid clearance. Many of the particulate imaging systems used to date are designed exclusively for blood pool and lymphatic system imaging. The use of targeting imaging systems has the potential to increase accumulation at the target site, leading to a higher sensitivity and thus enabling molecular imaging outside the blood pool and lymphatic system. It is envisaged that targeted nanoparticles which contain both therapeutic and imaging agents could enable the use of a single vehicle for diagnosis, treatment and follow-up monitoring of a disease.

Polymeric nanoparticles have received a great deal of attention in the field of medicine, in particular those comprising biodegradable polymers such as poly(lactic acid), poly(glycolic acid) and poly(alkyl cyanoacrylate), however those developed to date have limited effectiveness because of high clearance rates and their propensity to distribute through the whole body, including into healthy tissue. Controlled delivery of an active agent using nanoparticles therefore remains a challenge and there is a need for the development of biocompatible compositions capable of extended delivery of active agents which provide prolonged circulation time and increased stability compared to administration of the active agent alone.

Long circulating nanoparticles, i.e. those with enhanced stability in the circulatory system, have been investigated in this regard and go some way to addressing these issues. These types of nanoparticles have a hydrophilic shell around the nanoparticles, known as a stealth corona, which is typically provided by a hydrophilic polymer and leads to an increase in the blood circulation half-life of the nanoparticle, vastly increasing circulation times. The hydrophilic shell mimics water and acts as an immunoprotective layer, rendering the nanoparticles relatively "invisible" to the immune system, enabling them to avoid uptake by phagocytic cells. Stealth-structured nanoparticles are well known and have been prepared with a variety of nanoparticle cores and with a range of polymeric shells, as discussed in Nicolas and Couvreur in *Rev. Nanomed. Nanobiotechnol.*, 2009, 1, 111-127, Storm et al., Adv Drug Deliv Rev 1995, 17: 31-48 and Stolnik, Illum & Davis, Adv Drug Deliv Rev 1995, 16: 195-214. Their use in the encapsulation of therapeutic agents has also been described in, for example, US 2002/0034474. A commercially available example is Doxil®, which comprises pegylated liposomes containing doxorubicin.

However, there remains a need to combine these extended circulation times with targeted delivery so that accumulation in healthy tissue is minimised, thus reducing adverse side effects. The incorporation of targeting moieties onto the surface of stealth nanoparticles is not a simple feat, however, because the presence of these additional groups has the potential to disrupt the stealth structure. As a result, known methods for the preparation of stealth nanoparticles are not easily adapted to successfully produce targeting stealth nanoparticles.

Many methods for preparing nanoparticles are known, such as emulsion polymerisation and nanoprecipitation. Anionic emulsion polymerisation is described in, for example, US 2008/0138418.

Miniemulsion processes are known for the production of nanoparticles with average sizes typically in the range 1-1000 nm, most typically 50-500 nm as disclosed e.g. in Landfester in *Macromol. Rapid Comm.* 2001, 22, 896-936 and Landfester et al in *Macromolecules* 1999, 32, 5222-5228. The method was first described in 1972 by Ugelstad and Vanderhoff. The miniemulsion technique for the preparation of polymeric nanoparticles is a technology by which a dispersion is prepared, by converting a stable nanoemulsion of a dispersed phase in a continuous phase into a nanoparticle dispersion by polymerisation reactions. The technology involves mixing the various components in the dispersed phase before emulsification with the continuous phase takes place, resulting in the production of an emulsion in which each droplet has an identical composition of active agent and monomers. All types of polymerisation reactions may be applied in these droplet nanoreactors. In the case of the present invention, oil-in-water miniemulsions and anionic polymerisation at the droplet interface, commonly started by adding an initiator to the continuous phase, are the preferred embodiments. The particles formed are typically identical or almost identical to the droplets from which they are prepared, in terms of size and size distribution, resulting in high reproducibility of the process.

Miniemulsions are usually stabilised by a surfactant and a co-stabiliser, the latter often referred to as "hydrophobe". The co-stabiliser contributes to the osmotic stabilisation of the emulsion by increasing the osmotic pressure, which counteracts the capillary or Kelvin pressure due to surface tension of the droplets and reduces Ostwald ripening by minimising diffusion of the monomer from small to large droplets.

In conventional emulsions, the polymers are directly formed from the solution containing monomers, while, in a miniemulsion process, two liquid phases are first brought into contact and an emulsion is formed subsequently. Another difference is that conventional emulsion polymerisation processes result in suspensions containing only about 1% of nanoparticles, while the miniemulsion process allows a solid content of nanoparticles of 15-25% or more, which is important in terms of up-scaling and production costs. Conventional emulsion processes result in nanospheres, which are matrix systems, where the drug is physically and uniformly dispersed in the polymer, while miniemulsion processes combined with interfacial polymerisation reactions result in nanocapsules, which are vesicular systems in which the drug is solubilized in a liquid core, surrounded by a thin polymer layer. It should therefore be appreciated that conventional emulsions and miniemulsion processes are quite different and that the products produced therefrom are structurally distinct.

In US 2008/182776 and US 2010/015165 miniemulsion polymerisation processes for the preparation of poly(alkyl cyanoacrylate) nanoparticles are described. The polymerisation initiators used are surfactants (pluronics) and primary or secondary amines, respectively, although, in general, any nucleophilic compound, containing for example hydroxyl or amino groups may be used. Examples of initiators include sodium hydroxide, amino acids (e.g. glycine) and polyethyleneglycols. Initiation may also take place via alteration of the pH as discussed in, for example, US 2009/0297613.

Most of the known processes for the preparation of targeting stealth nanoparticles and the only known process for the preparation of targeting stealth nanoparticles of polyalkyl cyanoacrylates involve several consecutive steps: encapsulation of the active agent together with the introduction of the stealth layer, followed by introduction of targeting moieties which is usually by way of activation and coupling steps. Alternatively, the targeting moiety may be added to the component which will form the stealth layer separately prior to nanoparticle formation. See, e.g. US 2010/0104645. Precise control of biomaterial structure and composition, in addition to complete characterisation of the products of each step in the synthesis is required in order to comply with the necessary regulations governing clinical acceptance. As a result, these conventional preparation methods are very costly and time consuming.

It is therefore desirable, and hence an object of the present invention, to develop a new, more efficient method for the preparation of targeting, stealth nanoparticles which are capable of delivering a therapeutic agent to a desired target without compromising the longer circulation times associated with the stealth structure. In particular, a process which involves fewer steps would be desirable. Ultimately, it is desired if the process is suitable for commercial applications.

The present inventors have surprisingly found that this may be achieved by utilising a miniemulsion process in combination with a particular class of polyalkylene glycol derivatives. Specifically, they have developed a process in which at least one polyalkylene glycol covalently attached to a targeting moiety is used, preferably in combination with a polyalkylene glycol not attached to a targeting moiety, thus enabling the simultaneous introduction of a targeting group and formation of a stealth corona. Unexpectedly, this was possible in a single polymerisation step, thereby reducing characterisation and production costs remarkably, ideally without compromising the long-circulating properties of the nanoparticle.

SUMMARY OF THE INVENTION

Thus, viewed from one aspect, the invention provides a process for the preparation of targeting nanoparticles of a poly(alkyl cyanoacrylate) homopolymer or copolymer, wherein said method comprises, in a single step, the anionic polymerisation of an oil-in-water miniemulsion, wherein said miniemulsion comprises (i) polymerisable monomers comprising at least one alkyl cyanoacrylate monomer;

(ii) at least two polyalkylene glycols selected from the group consisting of polyethylene glycols (PEG) and polypropylene glycols (PPG) or mixtures thereof, wherein at least one of said polyalkylene glycols is covalently attached to a targeting moiety; and (iii) optionally one or more active agents.

Viewed from an alternative aspect, the invention provides a process for the preparation of targeting nanoparticles of a poly(alkyl cyanoacrylate) homopolymer or copolymer, wherein said method comprises adding at least two polyalkylene glycols selected from the group consisting of polyethylene glycols (PEG) and polypropylene glycols (PPG) or mixtures thereof, to an oil-in-water miniemulsion, wherein said miniemulsion comprises (i) polymerisable monomers comprising at least one alkyl cyanoacrylate monomer; and (ii) optionally one or more active agents;

and polymerising the resulting mixture by anionic polymerisation.

Viewed from another aspect, the invention provides targeting nanoparticles of a poly(alkyl cyanoacrylate) homopolymer or copolymer, produced by the process as hereinbefore described.

Viewed from another aspect, the invention provides pharmaceutical compositions comprising the targeting nanoparticles as hereinbefore described.

Viewed from another aspect, the invention provides the use of the targeting nanoparticles as hereinbefore described in medicine.

DETAILED DESCRIPTION OF THE INVENTION

The present invention describes a process for the preparation of targeting nanoparticles of a poly(alkyl cyanoacrylate) homopolymer or copolymer, wherein said method comprises, in a single step, the formation of said nanoparticles by anionic polymerisation of an oil-in-water miniemulsion.

Miniemulsion

As used herein, the term "miniemulsion" means a specific type of emulsion comprising stable droplets with typical mean sizes within the range 50 to 500 nm. The particle size is influenced by a number of factors, including the amount of surfactant present, the viscosity of the system as a whole and the shear rate used to produce the droplets. Typical particle size distribution curves (measured using, for example, dynamic light scattering) for miniemulsions are Gaussian in shape and are relatively narrow. The miniemulsions of the present invention preferably have a polydispersity index (PDI) of 0.3 or less, more preferably 0.2 or less, such as about 0.1.

Miniemulsions are ideally stabilised by the presence of a surfactant and a co-stabiliser, the latter often referred to as "hydrophobe". The co-stabiliser contributes to the osmotic stabilisation of the emulsion by increasing the osmotic pressure, which counteracts the capillary or Kelvin pressure due to surface tension of the droplets and reduces Ostwald ripening. Ostwald ripening refers to the process by which molecules diffuse from small droplets to large ones through the continuous phase. This process disrupts the emulsion structure. Miniemulsions may be direct (oil-in-water) or inverse (water-in-oil) although for the purposes of the present invention, the term "miniemulsion" may be considered to refer only to direct miniemulsions. In the miniemulsions of the invention therefore, water forms the continuous phase. The oil phase typically contains the monomers used in the anionic polymerisation, the co-stabiliser and the active agent, if present.

As discussed above, miniemulsions and miniemulsion polymerisation for the preparation of nanoparticles are known in the art.

The miniemulsion may be prepared by any known method in the art, such as that described in US 2009/0297613. Processes typically involve forming the oil and water phases, mixing these and subjecting the mixture to high shear forces, e.g. ultrasonication or homogenisation, to form a stable emulsion of oil droplets containing the monomer with a stabiliser/surfactant on the surface, and then subsequently adding a hydrophilic initiator. Polymerisation of the monomer droplets then occurs by initiation at the droplet interface to form polymeric particles which have the same size as the droplets before polymerisation. The hydrophilic initiator is attached to the surface of the particles. It should be apparent to the skilled worker that the miniemulsion polymerisation processes described in the context of the present invention are quite distinct from emulsion polymerisation processes whereby polymeric nanoparticles are formed directly from a solution of the monomers in a solvent and from emulsion processes using pre-made polymers, whereby the polymeric nanoparticles are formed by self-assembly of these pre-made polymers.

The miniemulsions of the present invention comprise at least two components: polymerisable monomers comprising at least one alkyl cyanoacrylate monomer; and at least two polyalkylene glycols selected from polyethylene glycols (PEGs) and polypropylene glycols (PPGs), or mixtures thereof, wherein at least one of said polyalkylene glycols is covalently attached to a targeting moiety. The miniemulsions may also optionally comprise one or more active agents. In one embodiment of the invention, at least one of said polyalkylene glycols initiates the anionic polymerisation of the polymerisable monomers.

The miniemulsions of the invention may comprise a surfactant. Any typical surfactant known in the art may be used, however preferable surfactants include fatty acids of glycerols, sorbitol and other multifunctional alcohols, poloxamers, poloxamines, polysorbates, polyoxyethylene ethers and polyoxyethylene esters, ethoxylated triglycerides, ethoxylated phenols and diphenols, metal salts of fatty acids, metal salts of fatty alcohol sulfates, sodium lauryl sulfate, metal salts of sulfosuccinates and mixtures thereof. Particularly preferred surfactants include polyoxyethylene ethers and polysorbates.

The surfactant preferably comprises 0.05 to 5 wt % of the miniemulsion, more preferably 0.1 to 2 wt %.

In addition to these components, the miniemulsion may further comprise a co-stabiliser in the oil phase. The co-stabiliser is typically highly water insoluble, i.e. has a solubility of less than $5 \times 10^{-5}$ molL$^{-1}$, more preferably less than $5 \times 10^{-6}$ molL$^{-1}$ and still more preferably less than $5 \times 10^{-7}$ molL$^{-1}$ and may be any substance which is compatible with the polymerisable monomers, such as a hydrocarbon, silane, organosilane, fatty acid ester, oil (e.g. plant oil), hydrophobic dye or lipid. Examples of suitable co-stabilisers include hexadecane, cetyl alcohol, miglyol and olive oil. Particularly preferred co-stabilisers include miglyols and plant oils. In an alternative embodiment, the active agent may perform the role of the co-stabiliser.

The co-stabiliser preferably comprises 0.5 to 5 wt % of the oil phase, more preferably 1 to 3 wt %.

In a further embodiment the miniemulsion used in the process of the current invention comprises a crosslinker (especially a biodegradable crosslinker), preferably in the oil phase (i.e. the discontinuous phase). The crosslinker is preferably an anhydride or an acrylate such as ethylene glycol dimethacrylate, methacrylic anhydride or methylene dimethacrylate.

The oil phase content of the miniemulsions of the invention is preferably in the range 1 to 50 wt %, more preferably 15-25 wt %. The skilled man will understand that the oil phase content of the mini-emulsions of the present invention may also be referred to as the solid content. Thus, the terms "solid content" and "oil phase content" are interchangeable in the context of the present invention.

Polymerisable Monomers

The polymerisable monomers in the miniemulsion of the present invention comprise at least one alkyl cyanoacrylate monomer. These are biodegradable monomers whose use in the preparation of nanoparticles has been widely reported. The alkyl cyanoacrylate may be a monofunctional or difunctional acrylate i.e. containing a single or multiple acrylate functionalities. Any straight or branched chain alkyl cyanoacrylate monomer or derivative thereof may be used, however preferred monomers are those of $C_1$-$C_{10}$ alkyl cyanoacrylates, more preferably $C_2$-$C_8$ alkyl cyanoacrylates. A single monomer may be used or mixtures of different alkyl cyanoacrylates may be used. Preferred alkyl cyanoacrylates include ethyl cyanoacrylate, butyl (n-butyl) cyanoacrylate, isohexyl cyanoacrylate, octyl cyanoacrylate and derivatives and mixtures thereof. Butyl cyanoacrylate, isohexyl cyanoacrylate and octyl cyanoacrylate are particularly preferred.

Without wishing to be bound by theory, it is believed that the nature of the monomers influences the degradation rate of the miniemulsion. The more hydrophobic the monomer (i.e. the longer the alkyl chain), the slower the degradation rate, probably due to a lower water activity in more hydrophobic polymers. It is therefore another embodiment of the invention to use a mixture of alkyl cyanoacrylates of differing chain length, e.g. one with a short alkyl chain and one with a long alkyl chain such as butyl cyanoacrylate mixed with isohexyl cyanoacrylate or octyl cyanoacrylate.

In one embodiment, a cyanoacrylate homopolymer is used, i.e. formed from a single monomer.

The alkyl cyanoacrylate monomers are preferably present in an amount of 1 to 100 wt %, more preferably 75-100 wt %, even more preferably 95-100 wt % of the total amount of monomers.

In addition to the alkyl cyanoacrylate monomers, other co-monomers may also be present in the miniemulsions of the invention. It is preferable if these co-monomers are also biocompatible or biodegradable. Suitable co-monomers include, but are not limited to acrylates, vinyl esters, vinyl ethers, vinyl epoxides, cyclic siloxanes and lactones.

The polymerisable monomers preferably comprise 25 to 99.5 wt % of the oil phase, more preferably 30 to 70 wt %.

Preferably, the polymerisable monomers comprise 0.5 to 50 wt % of the miniemulsion, e.g. 5 to 18 wt %.

Polyalkylene Glycols

The miniemulsions of the present invention comprise at least two polyalkylene glycols selected from the group consisting of polyethylene glycols (PEG) and polypropylene glycols (PPG) or mixtures thereof, wherein at least one of said polyalkylene glycols is covalently attached to a targeting moiety. At least one of the polyalkylene glycols preferably initiates the anionic polymerisation reaction.

The polyalkylene glycols are usually added to the continuous phase of the miniemulsion, i.e. the water phase. Preferably, at least one of the polyalkylene glycols is covalently attached to a targeting moiety and at least one is not attached to a targeting moiety. It is especially preferred if the polyalkylene glycols are so water-soluble that a homogeneous solution may be prepared to add to the miniemulsion.

By the term "polyethylene glycol" (PEG) we mean any polymer containing mostly ethylene oxide repeating units, i.e. —$CH_2$—$CH_2$—O— units. Typical polyethylene glycols have a molecular mass less than 20000 g/mol, preferably less than 10000 g/mol. By the term "polypropylene glycol" (PPG) we mean any polymer containing mostly propylene oxide repeating units, i.e. —$CH_2$—$CH_2$—$CH_2$—O— units.

The polyalkylene glycols may have a hydroxy or amino end group, or a mixture thereof. The polyalkylene glycols are water soluble. By water soluble we mean that they must have a solubility in water which is high enough to enable the formation of a homogenous solution in water, which may then be added to the miniemulsion, i.e. a solubility of more than 10 g/L at RTP.

Examples of suitable polyalkylene glycols include polyethylene glycol and polypropylene glycol homopolymers and copolymers thereof. It should be noted that the term "polyethylene glycol" is intended to cover polysorbates (e.g. polysorbate 80). Most importantly, the copolymers may be block copolymers. Example copolymers include poly(propylene glycol)-poly(ethylene glycol) block copolymers, polyalkylamine-polyalkylene glycol block copolymers, lipid-polyalkylene glycol block copolymers and polylysine-polyalkylene glycol block copolymers.

The length of the blocks of each polymer may be varied so as to alter the properties of the copolymer, with the proviso that the copolymer remains water soluble. Increasing PPO content for example, reduces water solubility. In one embodiment, there is preferably a hydroxyl or amino end group directly attached to the PPO. Preferably the end group is an amino end group.

Preferably, the ratio of polyethylene glycol units to PPO units is in the range 1:5 to 5:1, such as 1:1. Each block may contain 2-40 monomer units. It is further preferred however if polyethylene glycol units are in excess.

Typical molecular weights for the polyalkylene glycol-PPO block copolymers of the invention are lower than 20 000 g/mol, preferably lower than 10 000 g/mol, such as 1000 to 8000.

The combination of a polyalkylene glycol covalently attached to a targeting moiety with a polyalkylene glycol not attached to a targeting moiety surprisingly enables the introduction of targeting moieties onto long-circulating nanoparticles during the polymerisation step, thereby facilitating a facile single-step process for the preparation of targeting stealth nanoparticles. This is therefore a preferable embodiment of the invention. Since polyalkylene glycols both with and without targeting moieties are present in the stealth corona the nanoparticles have the potential to possess targeting abilities whilst remaining relatively "invisible", thus avoiding rapid clearance. This is thought to be possible by way of varying the chain lengths of the polyalkylene glycols so as to optimise both targeting and stealth properties.

It is preferred if a polyethylene glycol is used, i.e. one in which polyethylene glycol units are present in the majority and it is preferred if that polyethylene glycol further comprises a hydrophobic component so as to optimise properties and enable efficient hydrophobic interaction with the monomers in the oil phase. Preferably the hydrophobic component is attached covalently to the polyethylene glycol, most preferably between the amino or hydroxyl end group and the rest of the polyethylene glycol moiety.

The hydrophobic component is typically an alkyl chain, polyether or a lipid. A particularly preferred hydrophobic component is polypropylene oxide (PPO) thus forming a polyethylene glycol/polypropylene glycol block copolymer. It should be understood that PPO is equivalent to PPG.

The targeting moiety may be any suitable moiety which targets, or causes the particle to become localised at specific locations within a subject. The targeting moiety should contain a functional group that can be reacted with the terminus opposite to the amino group terminus of the polyalkylene glycol. Suitable functional groups are those capable of forming a covalent bond with the polyalkylene glycol, such as amino, hydroxy, azide, alkyne and thio. The conjugation of the targeting moiety to the polyalkylene glycol may be performed by any method routinely used in the art, such as "click" chemistry.

Preferably, the targeting moiety has a molecular weight in the range 100 to 200 000 Da, more preferably 200 to 50000 Da, even more preferably 300 to 15000 Da.

It should be appreciated that a single targeting moiety or a mixture of different targeting moieties may be used.

Example targeting moieties are selected from the group consisting of an amino acid, protein, miniprotein (e.g. cysteine-knot miniprotein), peptide, antibody, antibody fragment, saccharide, carbohydrate, glycan, cytokine, chemikine, nucleotide, lectin, lipid, receptor, steroid, neurotransmitter, cell surface marker, cancer antigen, glycoprotein antigen, aptamer or mixtures thereof. Preferably, the targeting moiety or mixture of targeting moieties includes linear and cyclic peptides or cysteine-knot miniproteins.

In an alternative embodiment, example targeting moieties are selected from the group consisting of an amino acid, protein, peptide, antibody, antibody fragment, saccharide, carbohydrate, glycan, cytokine, chemikine, nucleotide, lectin, lipid, receptor, steroid, neurotransmitter, cell surface marker, cancer antigen, glycoprotein antigen, aptamer or mixtures thereof. Particularly preferred targeting moieties include linear and cyclic peptides.

Preferably, the amount of polyalkylene glycols (in total) is greater than 1 wt %, preferably greater than 5 wt % of the miniemulsion. The amount of polyalkylene glycols (in total) should preferably not exceed 15 wt %, more preferably 10 wt %. In preferred embodiments, the polyalkylene glycols covalently attached to a targeting moiety comprise 1 to 10 wt % of the total amount of polyalkylene glycols, preferably 1 to 5 wt %.

Active Agent

The active agent may be any agent which has a medicinal application, e.g. therapeutic agents or imaging agents. The active agent may be water soluble or water insoluble, preferably water insoluble. Where the active agent is water soluble it is typically added as a fine powder in an oil. In a preferred embodiment, the active agent comprises 1 to 75 wt % of the oil-phase, more preferably 30-60 wt %.

Example therapeutic agents, which of course do not restrict the present invention, include chemotherapeutic agents, diagnostic agents, antineoplastic agents, prophylactic agents, neutraceutical agents, antibiotics, antiviral agents, anti-inflammatory agents, small molecule kinase inhibitors, nucleic acids, proteins, peptides, lipids, carbohydrates, hormones, metals, ceramics, drugs, vaccines, immulogical agents, and mixtures thereof.

Preferred therapeutic agents include doxorubicin, gemcitabine, daunorubicine, procarbazine, docetaxel, paclitaxel, cabazitaxel, 5-fluorouracil, mitomycin, cytarabine, etoposide, methotrexate, vinblastine, vincristine, bleomycin, mitoxantrone, mitoxantrone hydrochloride, aldesleukin, asparaginase, busulfan, carboplatin, cladribine, camptothecin, dacarbazine, ftorafur, 5'deoxyfluorouridine, eniluracil, deoxycytidine, 5-azacytosine, 5-azadeoxycytosine, allopurinol, 2-chloroadenosine, trimetrexate, aminopterin, methylene-10-deazaaminopterin, cisplatin, oxaliplatin, picoplatin, tetraplatin, satraplatin, platinum-DACH, ormaplatin, epirubicin, etoposide phosphate, 9-aminocamptothecin, vindesine, L-phenylalanine mustard, 6-mercaptopurine, 6-thioguanine, amsacrine, karenitecin, acyclovir, valacyclovir, ganciclovir, amantadine, rimantadine, lamivudine, zidovudine, bevacizumab, trastuzumab, rituximab, sirolimus, temsirolimus, everolimus, imatinib, sorafenib, sunitinib, N-(4-((3-(2-aminopyrimidin-4-yl)pyridin-2-yl)oxy)phenyl)-4-(4-methylthiophen-2-yl)phthalazin-1-amine (AMG900), protein kinase D1 inibitors, protein kinase D2 inhibitors, protein kinase D3 inhibitors, 12-(2-Cyanoethyl)-6,7,12,13-tetrahydro-13-methyl-5-oxo-5H-indolo[2,3-a]pyrrolo[3,4-c]carbazole (Go6976), N-[2-(p-Bromocinnamylamino)ethyl]-5-isoquinolinesulfonamide (H89) and combinations thereof.

Alternatively, preferred therapeutic agents include doxorubicin, gemcitabine, daunorubicine, procarbazine, docetaxel, paclitaxel, cabazitaxel, 5-fluorouracil, mitomycin, cytarabine, etoposide, methotrexate, vinblastine, vincristine, bleomycin, mitoxantrone, mitoxantrone hydrochloride, aldesleukin, asparaginase, busulfan, carboplatin, cladribine, camptothecin, dacarbazine, ftorafur, 5'deoxyfluorouridine, eniluracil, deoxycytidine, 5-azacytosine, 5-azadeoxycytosine, allopurinol, 2-chloroadenosine, trimetrexate, aminopterin, methylene-10-deazaaminopterin, oxaliplatin, picoplatin, tetraplatin, satraplatin, platinum-DACH, ormaplatin, epirubicin, etoposide phosphate, 9-aminocamptothecin, vindesine, L-phenylalanine mustard, 6-mercaptopurine, 6-thioguanine, amsacrine, karenitecin, acyclovir, valacyclovir, ganciclovir, amantadine, rimantadine, lamivudine, zidovudine, bevacizumab, trastuzumab, rituximab, sirolimus, temsirolimus, everolimus, imatinib, sorafenib, sunitinib, N-(4-((3-(2-aminopyrimidin-4-yl)pyridin-2-yl)oxy)phenyl)-4-(4-methylthiophen-2-yl)phthalazin-1-amine (AMG900), protein kinase D1 inibitors, protein kinase D2 inhibitors, protein kinase D3 inhibitors, 12-(2-Cyanoethyl)-6,7,12,13-tetrahydro-13-methyl-5-oxo-5H-indolo[2,3-a]pyrrolo[3,4-c]carbazole (Go6976), N-[2-(p-Bromocinnamylamino)ethyl]-5-isoquinolinesulfonamide (H89) and combinations thereof.

Particularly preferable therapeutic agents are docetaxel, cabazitaxel, paclitaxel, 5-fluorouracil, sorafenib, AMG900, temsirolimus and everolimus.

Other highly preferable therapeutic agents include carboplatin, oxaliplatin, picoplatin, tetraplatin, satraplatin, cisplatin, platinum-DACH and ormaplatin.

Example imaging agents include metals (e.g. cobalt, iron, gold), metal salts (e.g. iron oxide, gadolinium salts), near infrared dyes, PET chelating agents, SPECT chelating agents, agents suitable for MRI or Raman spectroscopy, fluorescent dyes and radiopharmaceuticals.

Polymerisation

The processes according to the invention comprise the preparation of targeting nanoparticles of a poly(alkyl cyanoacrylate) homopolymer or copolymer, wherein said method comprises, in a single step, the anionic polymerisation of an oil-in-water miniemulsion, wherein said miniemulsion comprises (i) polymerisable monomers comprising at least one alkyl cyanoacrylate monomer;

(ii) at least two polyalkylene glycols selected from the group consisting of polyethylene glycols (PEG) and polypropylene glycols (PPG) or mixtures thereof, wherein at least one of said polyalkylene glycols is covalently attached to a targeting moiety; and (iii) optionally one or more active agents.

The miniemulsion may be prepared by the addition of said at least two polyalkylene glycols to an oil-in water miniemulsion comprising said at least one alkyl cyanoacrylate monomer and optionally said one or more active agents. In a preferred embodiment, this addition step and the anionic polymerisation steps are performed consecutively, i.e. the anionic polymerisation step is carried out immediately (e.g. 0-10 minutes, such as 0-5 minutes) after the addition step.

Viewed from an alternative aspect, the processes of the invention comprise the preparation of targeting nanoparticles of a poly(alkyl cyanoacrylate) homopolymer or copolymer, wherein said method comprises adding at least two polyalkylene glycols selected from the group consisting of polyethylene glycols (PEG) and polypropylene glycols (PPG) or mixtures thereof, to an oil-in-water miniemulsion, wherein said miniemulsion comprises (i) polymerisable monomers comprising at least one alkyl cyanoacrylate monomer; and (ii) optionally one or more active agents;

and polymerising the resulting mixture by anionic polymerisation.

Preferably, at least one of said polyalkylene glycols initiates the anionic polymerisation reaction.

In all aspects of the invention, said nanoparticles are preferably stealth nanoparticles.

The processes of the invention allow, in a single step, the simultaneous polymerisation of the monomers, formation of the "stealth corona" and introduction of the targeting moiety onto the surface of the nanoparticles, which was not previously possible using the methods of the prior art. The result is the generation of nanoparticles which are able to remain relatively "invisible" to clearance systems within the body, thereby having enhanced circulation times, whilst possessing targeting properties which enhance their efficacy.

The miniemulsion is typically prepared by adding an oil phase containing the monomer(s) and co-stabiliser to an aqueous solution containing a surfactant and subjecting this to high shear forces, e.g. by ultrasonication, to form oil droplets containing the monomer(s) in water. The droplets formed at this stage are a miniemulsion. This may then be added, to a third, typically aqueous, solution containing the at least two polyalkylene glycols. Preferably the polymerisation reaction is carried out at low pH, e.g. pH 1-7. It is preferable if the polymerisation reaction is a carried out at room temperature, e.g. 15 to 30° C. The resulting blend is a dispersion.

Preferably, at least one of the polyalkylene glycols initiates an anionic polymerisation process. Where the polyalkylene glycol initiator has an amino or hydroxide end group, initiation is preferably achieved through nucleophilic attack on the monomer double bond resulting in an anionic or zwitter-ionic polymerisation reaction.

Such processes are well known in the art and hence the mechanisms involved will be well known to the skilled worker.

In a particularly preferred embodiment, the anionic polymerisation is combined with radical polymerisation by way of the presence of an additional initiator. This additional initiator will typically be oil soluble and hence commonly be in the oil phase of the miniemulsion, i.e. within the oil droplet. Where these two types of polymerisation are combined, the process of the invention is modified so as to incorporate an increase in temperature, which initiates the radical polymerisation. Typical radical polymerisation initiators include peroxides and azo compounds such as azobisdimethyl valeronitril and azoisobutyronitrile.

In one embodiment, the process of the invention may be modified to include crosslinking of the alkyl cyanoacrylate monomers and, if present, co-monomers. This can be facilitated by incorporating a crosslinker, preferably a radically polymerisable crosslinker, into the miniemulsion, preferably within the oil phase. The crosslinker will, in general, be hydrolysed on contact with the aqueous phase, thereby controlling drug release rates and the biodegradability of the nanoparticles. Example crosslinkers include anhydrides or acrylates such as ethylene glycol dimethacrylate, methacrylic anhydride or methylene dimethacrylate.

The processes of the present invention may comprise a further step wherein the nanoparticles are isolated. This may be carried out by any known method in the art.

In a further embodiment, the processes of the invention may include a step of raising the temperature (to e.g. 50° C.) so as to ensure all residual monomer reacts and/or to initiate crosslinking.

Targeting efficiency and drug release may be varied by varying the amount, type and length of both the polyalkylene glycol(s) attached to the targeting moiety and the polyalkylene glycol(s) not attached to the targeting moiety, or by altering the monomer composition.

Nanoparticles

The nanoparticles produced by the processes of the present invention are different in structure to those produced by emulsion polymerisation. In particular, nanoparticles made by emulsion polymerisation comprise a polymer matrix with any active agent being physically and uniformly dispersed in that matrix. Conversely, nanoparticles made by miniemulsion interfacial polymerisation are vesicular systems, which contain the active agent in the core of the nanoparticle, surrounded by a polymer shell.

The nanoparticles produced in accordance with the current invention may be formulated as a pharmaceutical composition comprising the nanoparticles together with one or more pharmaceutically acceptable carriers, diluents or excipients. Such carriers, diluents and excipients are well known in the art. The pharmaceutical compositions may also comprise additional active agents.

Uses

The nanoparticles and compositions thereof may be used in medicine, in particular in drug delivery and imaging applications. Hence, the present invention relates to nanoparticles according to the present invention for use in medicine. In a further embodiment, the present invention relates to the nanoparticles according to the current invention for use in the treatment or prevention, or the diagnosis of particular disorders and diseases. Examples of disorders or diseases which can be treated or prevented in accordance with the present invention include cancer, such as lung cancer, breast cancer, prostate cancer, head and neck cancer, ovarian cancer, skin cancer, testicular cancer, pancreatic cancer, colorectal cancer, kidney cancer, cervical cancer, gastrointestinal cancer and combinations thereof.

The nanoparticles or compositions thereof are preferably administered in a therapeutically effective amount. A "therapeutically effective amount" refers to an amount of the nanoparticles necessary to treat or prevent the particular disease or disorder. Any route of administration may be used to deliver the nanoparticles to the subject. Suitable administration routes include intramuscular injection, transdermal administration, inhalation, topical application, oral administration, rectal or vaginal administration, intratumural administration and parenteral administration (e.g. intravenous, peritoneal, intra-arterial or subcutaneous). The preferable route of administration is injection.

The exact dosage and frequency of administration depends on the particular nanoparticles, active agent and targeting agents used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the nanoparticles according to the instant invention.

EXAMPLES

Preparation of Nanoparticles

Example 1

Stealth Particles with Approximately 1% RGD Targeting Moieties (Short PEG with RGD Embedded in PEG Layer) Using the Miniemulsion Method Solution 1 (PEG/initiator and targeting ligand): 330 mg of short (approx. 15 PEG units) mPEG-PPO—$NH_2$ (MW 935, m=OMe protecting group), 280 µl of a 70 mg/ml solution of peptide-PEG-PPO ($H_2N$—PPO-$PEG_{15}$-RGDfK) and 3.2 g of distilled water were mixed in a glass vial, pH adjusted to pH 6 with 5M HCl and degassed using $N_2$ for 15 minutes.

Solution 2 (monomer phase): 0.6 g of n-butyl cyanoacrylate (monomer, Henkel Loctite, Ireland), 12 mg of hexadecane (co-stabilizer), 5 mg of Azobisdimethyl valeronitril (V65, radical initiator for crosslinking, Wako Chemicals), 39 mg of Ethylene glycol dimethacrylate (EGDMA, crosslinker, Fluka) and 0.5 mg of Nile red (fluorescent dye, Fluka) were thoroughly mixed in a glass vial.

Solution 3 (stabilizer): 10 mg of Sodium dodecyl sulfate (SDS, Merck) were dissolved in 2.4 g of distilled water and pH adjusted to pH 4.5 using 0.1 M HCl. Solution 2 and 3 were mixed for 30 seconds in a 5 ml glass vial placed on ice using a magnetic stirrer. The oil-in water emulsion was immediately sonicated for 3 minutes (6×30 sec intervals) on ice (Branson digital sonifier 450 CE, 25% amplitude).

The emulsion was added to the glass vial containing Solution 1 immediately after sonication and polymerized over night at room temperature on rotation (15 rpm). The pH was neutralized and the temperature increased to 50° C. to initiate crosslinking of the polymer. After 8 hours the solution was dialyzed (Spectra/Por dialysis membrane MWCO 12-14000) extensively against distilled water at room temperature to remove surfactant and unreacted PEG. The distilled water was renewed until the conductivity of the surrounding solution had reached the same value as for pure distilled water.

The particle size and their zetapotential was determined using Malvern Nano Series zetasizer.

The above mentioned method resulted in PEGylated, targeted nanoparticles of 124 nm (z-average diameter) with a polydispersity index of 0.19, zetapotential of −14 mV and nanoparticle concentration of 1.94% (w/w).

Example 2

Stealth Particles with Approximately 5% RGD Targeting Moieties (Long PEG with RGD Sticking Out of PEG Layer) Using the Miniemulsion Method Solution 1 (PEG/initiator and targeting ligand): 460 mg of long (approx. 20 PEG units) mPEG-PPO—$NH_2$ (MW 1300, m=OMe protecting group), 1.95 ml of a 70 mg/ml solution of peptide-PEG-PPO ($H_2N$—PPO-$PEG_{15}$-RGDfK) and 1.55 g of distilled water were mixed in a glass vial, pH adjusted to pH 6 with 5M HCl and degassed using $N_2$ for 15 minutes.

Solutions 2 and 3 are as described in Example 1.

Solution 2 and 3 were mixed for 30 seconds in a 5 ml glass vial placed on ice using a magnetic stirrer. The oil-in water emulsion was immediately sonicated for 3 minutes (6×30 sec intervals) on ice (Branson digital sonifier 450 CE, 25% amplitude).

The emulsion was added to the glass vial containing Solution 1 immediately after sonication and polymerized over night at room temperature on rotation (15 rpm). The pH was neutralized and the temperature increased to 50° C. to initiate crosslinking of the polymer. After 8 hours the solution was dialyzed (Spectra/Por dialysis membrane MWCO 12-14000) extensively against distilled water at room temperature to remove surfactant and unreacted PEG. The distilled water was renewed until the conductivity of the surrounding solution had reached the same value as for pure distilled water.

The particle size and their zetapotential was determined using Malvern Nano Series zetasizer.

The above mentioned method resulted in PEGylated, targeted nanoparticles of 141 nm (z-average diameter) with a polydispersity index of 0.07, zetapotential of −12 mV and nanoparticle concentration of 0.84% (w/w).

Example 3

Stealth Particles without Targeting Moieties (Negative Control) Using the Miniemulsion Method Solution 1 (PEG/initiator): 330 mg of short (approx. 15 units) mPEG-PPO—$NH_2$ (MW 935, m=OMe protecting group) and 3.5 g of distilled water were mixed in a glass vial, pH adjusted to pH 6 with 5M HCl and degassed using $N_2$ for 15 minutes. Solutions 2 and 3 are as described in Example 1.

Solution 2 and 3 were mixed for 30 seconds in a 5 ml glass vial placed on ice using a magnetic stirrer. The oil-in water emulsion was immediately sonicated for 3 minutes (6×30 sec intervals) on ice (Branson digital sonifier 450 CE, 25% amplitude).

The emulsion was added to the glass vial containing Solution 1 immediately after sonication and polymerized over night at room temperature on rotation (15 rpm). The pH was neutralized and the temperature increased to 50° C. to initiate crosslinking of the polymer. After 8 hours the solution was dialyzed (Spectra/Por dialysis membrane MWCO 12-14000) extensively against distilled water at room temperature to remove surfactant and unreacted PEG. The distilled water was renewed until the conductivity of the surrounding solution had reached the same value as for pure distilled water.

The particle size and their zetapotential was determined using Malvern Nano Series zetasizer.

The above mentioned method resulted in PEGylated nanoparticles of 120 nm (z-average diameter) with a polydispersity index of 0.16, zetapotential of −22 mV and nanoparticle concentration of 2.13% (w/w).

Example 4

Stealth PBCA Particles with 1% RGD Targeting Moieties (Short PEG with RGD Embedded in PEG Layer) Using the Miniemulsion Method Solution 1 (PEG/initiator/stabilizer and targeting ligand): 50 mg of Kolliphor HS 15 (15 PEG units, MW 960, Sigma), 50 mg of Brij L23 (23 PEG units, MW 1225, Sigma), 0.85 mg of c(RGDfK(PEG-PEG)) (where PEG=8-Amino-3,6-Dioxaoctanoic Acid, MW 894, Peptides International, USA) and 8 ml of 0.1 M HCl were mixed in a glass vial.

Solution 2 (monomer phase): 0.75 g of n-butyl cyanoacrylate (monomer, Henkel Loctite, Ireland) and 13 mg of Miglyol 810N (co-stabilizer, Cremer, Germany) were thoroughly mixed in a glass vial.

Solution 1 and 2 were mixed for 30 seconds in a glass vial placed on ice using a magnetic stirrer. The oil-in-water emulsion was immediately sonicated for 3 minutes (6×30 sec intervals) on ice (Branson digital sonifier 450 CE, 60% amplitude). The emulsion was polymerized overnight at room temperature on rotation (15 rpm). The pH was increased by carefully adding 8 ml of 0.1 M NaOH during stirring. The solution was kept on rotation (15 rpm) for additional 5 hours at room temperature. The solution was dialyzed (Spectra/Por dialysis membrane MWCO 12-14000) extensively against 0.001 M HCl (pH 3) at room temperature to remove unreacted PEG. The dialysate was replaced 5 times.

The particle size and their zetapotential was determined using Malvern Nano Series zetasizer in 0.01 M phosphate buffer pH 7.

The above mentioned method resulted in PEGylated, targeted nanoparticles of 123 nm (z-average diameter) with a polydispersity index of 0.23, zetapotential of −2 mV and nanoparticle concentration of 2.6% (w/w) after dialysis.

Example 5

Stealth PBCA Particles with 5% RGD Targeting Moieties (Short PEG with RGD Embedded in PEG Layer) Using the Miniemulsion Method Solution 1 (PEG/initiator/stabilizer and targeting ligand): 50 mg of Kolliphor HS 15 (15 PEG units, MW 960, Sigma), 50 mg of Brij L23 (23 PEG units, MW 1225, Sigma), 42 mg of c(RGDfK(PEG-PEG)) (where PEG=8-Amino-3,6-Dioxaoctanoic Acid, MW 894, Peptides International, USA) and 8 ml of 0.1 M HCl were mixed in a glass vial.

Solution 2 (monomer phase): 0.75 g of n-butyl cyanoacrylate (monomer, Henkel Loctite, Ireland) and 13 mg of Miglyol 810N (co-stabilizer, Cremer, Germany) were thoroughly mixed in a glass vial.

Solution 1 and 2 were mixed for 30 seconds in a glass vial placed on ice using a magnetic stirrer. The oil-in-water emulsion was immediately sonicated for 3 minutes (6×30 sec intervals) on ice (Branson digital sonifier 450 CE, 60% amplitude). The emulsion was polymerized over night at room temperature on rotation (15 rpm). The pH was increased by carefully adding 8 ml of 0.1 M NaOH during stirring. The solution was kept on rotation (15 rpm) for additional 5 hours at room temperature. The solution was dialyzed (Spectra/Por dialysis membrane MWCO 12-14000) extensively against 0.001 M HCl (pH 3) at room temperature to remove unreacted PEG. The dialysate was replaced 5 times.

The particle size and their zetapotential was determined using Malvern Nano Series zetasizer in 0.01 M phosphate buffer pH 7.

The above mentioned method resulted in PEGylated, targeted nanoparticles of 117 nm (z-average diameter) with a polydispersity index of 0.23, zetapotential of −2 mV and nanoparticle concentration of 2.4% (w/w) after dialysis.

Example 6

Stealth PIHCA Particles with 5% RGD Targeting Moieties (Short PEG with RGD Embedded in PEG Layer) Using the Miniemulsion Method Solution 1 (PEG/initiator/stabilizer and targeting ligand): 50 mg of Kolliphor HS 15 (15 PEG units, MW 960, Sigma), 50 mg of Brij L23 (23 PEG units, MW 1225, Sigma), 42 mg of c(RGDfK(PEG-PEG)) (where PEG=8-Amino-3,6-Dioxaoctanoic Acid, MW 894, Peptides International, USA) and 8 ml of 0.1 M HCl were mixed in a glass vial.

Solution 2 (monomer phase): 0.75 g of isohexyl cyanoacrylate (monomer, Henkel Loctite, Ireland) and 13 mg of Miglyol 810N (co-stabilizer, Cremer, Germany) were thoroughly mixed in a glass vial.

Solution 1 and 2 were mixed for 30 seconds in a glass vial placed on ice using a magnetic stirrer. The oil-in-water emulsion was immediately sonicated for 3 minutes (6×30 sec intervals) on ice (Branson digital sonifier 450 CE, 60% amplitude). The emulsion was polymerized over night at room temperature on rotation (15 rpm). The pH was increased by carefully adding 8 ml of 0.1 M NaOH during stirring. The solution was kept on rotation (15 rpm) for additional 5 hours at room temperature. The solution was dialyzed (Spectra/Por dialysis membrane MWCO 12-14000) extensively against 0.001 M HCl (pH 3) at room temperature to remove unreacted PEG. The dialysate was replaced 5 times.

The particle size and their zetapotential was determined using Malvern Nano Series zetasizer in 0.01 M phosphate buffer pH 7.

The above mentioned method resulted in PEGylated, targeted nanoparticles of 140 nm (z-average diameter) with a polydispersity index of 0.22, zetapotential of −1 mV and nanoparticle concentration of 2.4% (w/w) after dialysis.

Example 7

Stealth POCA Particles with 5% RGD Targeting Moieties (Short PEG with RGD Embedded in PEG Layer) Using the Miniemulsion Method Solution 1 (PEG/initiator/stabilizer and targeting ligand): 50 mg of Kolliphor HS 15 (15 PEG units, MW 960, Sigma), 50 mg of Brij L23 (23 PEG units, MW 1225, Sigma), 42 mg of c(RGDfK(PEG-PEG)) (where PEG=8-Amino-3,6-Dioxaoctanoic Acid, MW 894, Peptides International, USA) and 8 ml of 0.1 M HCl were mixed in a glass vial.

Solution 2 (monomer phase): 0.75 g of octyl cyanoacrylate (monomer, Henkel Loctite, Ireland) and 13 mg of Miglyol 810N (co-stabilizer, Cremer, Germany) were thoroughly mixed in a glass vial.

Solution 1 and 2 were mixed for 30 seconds in a glass vial placed on ice using a magnetic stirrer. The oil-in-water emulsion was immediately sonicated for 3 minutes (6×30 sec intervals) on ice (Branson digital sonifier 450 CE, 60% amplitude). The emulsion was polymerized over night at room temperature on rotation (15 rpm). The pH was increased by carefully adding 8 ml of 0.1 M NaOH during stirring. The solution was kept on rotation (15 rpm) for additional 5 hours at room temperature. The solution was dialyzed (Spectra/Por dialysis membrane MWCO 12-14000) extensively against 0.001 M HCl (pH 3) at room temperature to remove unreacted PEG. The dialysate was replaced 5 times.

The particle size and their zetapotential was determined using Malvern Nano Series zetasizer in 0.01 M phosphate buffer pH 7.

The above mentioned method resulted in PEGylated, targeted nanoparticles of 163 nm (z-average diameter) with a polydispersity index of 0.26, zetapotential of 0 mV and nanoparticle concentration of 2.6% (w/w) after dialysis.

Example 8

Stealth PBCA Particles without Targeting Moieties (Negative Control) Using the Miniemulsion Method Solution 1 (PEG/initiator/stabilizer): 150 mg of Kolliphor HS 15 (15 PEG units, MW 960, Sigma), 150 mg of Brij L23 (23 PEG units, MW 1225, Sigma), 3 mg of Jeffamine M-1000 (MW 1000, Huntsman) and 25 ml of 0.1 M HCl were mixed in a glass vial.

Solution 2 (monomer phase): 2.25 g of n-butyl cyanoacrylate (monomer, Henkel Loctite, Ireland) and 40 mg of Miglyol 810N (co-stabilizer, Cremer, Germany) were thoroughly mixed in a glass vial.

Solution 1 and 2 were mixed for 30 seconds in a glass vial placed on ice using a magnetic stirrer. The oil-in-water emulsion was immediately sonicated for 3 minutes (6×30 sec intervals) on ice (Branson digital sonifier 450 CE, 60% amplitude). The emulsion was polymerized over night at room temperature on rotation (15 rpm). The pH was increased by carefully adding 25 ml of 0.1 M NaOH during stirring. The solution was kept on rotation (15 rpm) for additional 5 hours at room temperature. The solution was dialyzed (Spectra/Por dialysis membrane MWCO 12-14000) extensively against 0.001 M HCl (pH 3) at room temperature to remove unreacted PEG. The dialysate was replaced 5 times.

The particle size and their zetapotential was determined using Malvern Nano Series zetasizer in 0.01 M phosphate buffer pH 7.

The above mentioned method resulted in PEGylated, non-targeted nanoparticles of 121 nm (z-average diameter) with a polydispersity index of 0.11, zetapotential of −3 mV and nanoparticle concentration of 4.1% (w/w) after dialysis.

Example 9

Stealth PBCA Particles with 2% RGD Targeting Moieties (Short PEG with RGD Embedded in PEG Layer) Using the Miniemulsion Method Solution 1 (PEG/initiator): 300 mg of Jeffamine M-2070 (MW 2000, Huntsman) was dissolved in 7 ml of distilled water in a glass vial, and pH adjusted to pH 6 with 5M HCl.

Solution 2 (monomer phase): 1.5 g of n-butyl cyanoacrylate (monomer, Henkel Loctite, Ireland) and 27 mg of Miglyol 810N (co-stabilizer, Cremer, Germany) were thoroughly mixed in a glass vial.

Solution 3 (PEG/initiator/stabilizer and targeting ligand): 150 mg of Brij L23 (23 PEG units, MW 1225, Sigma) and 2.2 mg of c(RGDfK(PEG-PEG)) (where PEG=8-Amino-3, 6-Dioxaoctanoic Acid, MW 894, Peptides International, USA) were dissolved in 8 ml of 0.1 M HCl.

Solution 2 and 3 were mixed for 30 seconds in a glass vial placed on ice using a magnetic stirrer. The oil-in water emulsion was immediately sonicated for 3 minutes (6×30 sec intervals) on ice (Branson digital sonifier 450 CE, 60% amplitude). The emulsion was added to the glass vial containing Solution 1 immediately after sonication and polymerized over night at room temperature on rotation (15 rpm). The pH was increased by adding 8 ml of 0.1 M NaOH and the polymerization continued for additional 5 hours at room temperature on rotation (15 rpm). The solution was dialyzed (Spectra/Por dialysis membrane MWCO 12-14000) extensively against 0.001 M HCl (pH 3) at room temperature to remove unreacted PEG. The dialysate was replaced 5 times. The particle size and their zetapotential was determined using Malvern Nano Series zetasizer in 0.01 M phosphate buffer pH 7.

The above mentioned method resulted in PEGylated, targeted nanoparticles of 174 nm (z-average diameter) with a polydispersity index of 0.17, zetapotential of −3 mV and nanoparticle concentration of 3.2% (w/w) after dialysis.

Example 10

Stealth PBCA Particles without Targeting Moieties (as Control) Using the Miniemulsion Method Solution 1 (PEG/initiator): 1 g of Jeffamine M-2070 (MW 2000, Huntsman) was dissolved in 20 ml of distilled water in a glass vial, and pH adjusted to pH 6 with 5M HCl.

Solution 2 (monomer phase): 4.5 g of n-butyl cyanoacrylate (monomer, Henkel Loctite, Ireland) and 80 mg of Miglyol 810N (co-stabilizer, Cremer, Germany) were thoroughly mixed in a glass vial.

Solution 3 (PEG/initiator/stabilizer): 450 mg of Brij L23 (23 PEG units, MW 1225, Sigma) and 19 mg of Jeffamine M-1000 (MW 1000, Huntsman) were dissolved in 23 ml of 0.1 M HCl.

Solution 2 and 3 were mixed for 30 seconds in a glass vial placed on ice using a magnetic stirrer. The oil-in water emulsion was immediately sonicated for 3 minutes (6×30 sec intervals) on ice (Branson digital sonifier 450 CE, 60% amplitude). The emulsion was added to the glass vial containing Solution 1 immediately after sonication and polymerized over night at room temperature on rotation (15 rpm). The pH was increased to pH 5 and the polymerization continued for additional 5 hours at room temperature on rotation (15 rpm). The solution was dialyzed (Spectra/Por dialysis membrane MWCO 12-14000) extensively against 0.001 M HCl (pH 3) at room temperature to remove unreacted PEG. The dialysate was replaced 5 times. The particle size and their zetapotential was determined using Malvern Nano Series zetasizer in 0.01 M phosphate buffer pH 7.

The above mentioned method resulted in PEGylated, non-targeted nanoparticles of 178 nm (z-average diameter) with a polydispersity index of 0.19, zetapotential of −4 mV and nanoparticle concentration of 5.3% (w/w) after dialysis.

The invention claimed is:

1. A process for the preparation of nanoparticles of a poly(alkyl cyanoacrylate) homopolymer or copolymer, wherein said method comprises, in a single step, the anionic polymerisation of an oil-in-water miniemulsion, wherein said miniemulsion comprises:
   (i) at least one alkyl cyanoacrylate monomer;
   (ii) at least two different polyalkylene glycols independently selected from the group consisting of polyethylene glycols (PEG), polypropylene glycols (PPG), and copolymers thereof; and
   (iii) optionally one or more active agents,
   wherein at least one of said polyalkylene glycols initiates the single step anionic polymerisation reaction.

2. The process for the preparation of nanoparticles of a poly(alkyl cyanoacrylate) homopolymer or copolymer in claim 1, wherein at least one of said polyalkylene glycols is covalently attached to a targeting moiety.

3. The process as claimed in claim 1, wherein said miniemulsion is prepared by the addition of said at least two polyalkylene glycols to an oil-in water miniemulsion comprising said at least one alkyl cyanoacrylate monomer and optionally said one or more active agents.

4. The process as claimed in claim 3, wherein said nanoparticles are stealth nanoparticles.

5. The process as claimed in claim 3, wherein said miniemulsion further comprises a radically polymerisable crosslinker selected from the group consisting of an anhydride and an acrylate.

6. The process as claimed in claim 3, wherein said at least one alkyl cyanoacrylate monomer is selected from the group consisting of ethyl cyanoacrylate, butyl cyanoacrylate, isohexyl cyanoacrylate, octyl cyanoacrylate and derivatives and mixtures thereof.

7. The process as claimed in claim 3, wherein at least one of the polyalkylene glycols is a polyethylene glycol, optionally further comprising a hydrophobic component.

8. The process of claim 7, wherein at least one of the polyethylene glycols is a block copolymer of a polyethylene glycol block and polypropylene glycol block and wherein said copolymer comprises a hydroxy or amino end group attached to the polypropylene glycol block.

9. The process of claim 3 wherein the targeting moieties are selected from the group consisting of peptides, miniproteins, antibody fragments, affibody molecules, nanobodies and aptamers.

10. The process of claim 3, wherein the targeting moieties are selected from the group consisting of peptides, antibody fragments, affibody molecules, nanobodies and aptamers.

11. The process of claim 3 wherein the active agent is a therapeutic agent selected from the group consisting of docetaxel, cabazitaxel, paclitaxel, 5-fluorouracil, sorafenib, AMG900, temsirolimus or everolimus.

12. The process of claim 3 wherein the active agent is selected from the group consisting of carboplatin, oxaliplatin, picoplatin, tetraplatin, satraplatin, cisplatin, platinum-DACH and ormaplatin.

13. The process of claim 3 wherein the active agent is an imaging agent selected from the group consisting of metals, metal salts, near infrared dyes, fluorescent dyes, PET/SPECT chelating agents, agents suitable for MRI or Raman spectroscopy and radiopharmaceutical s.

* * * * *